United States Patent
Leoncavallo et al.

(10) Patent No.: US 6,976,398 B2
(45) Date of Patent: Dec. 20, 2005

(54) LIQUID SAMPLE COLLECTION SYSTEM

(75) Inventors: Richard A. Leoncavallo, Niagara Falls, NY (US); Peter K. Baird, Honeoye Falls, NY (US); Scott A. Harris, Rochester, NY (US)

(73) Assignee: Nalge Nunc International Corporation, Rochester, NY (US)

( * ) Notice: Subject to any disclaimer, the term of this patent is extended or adjusted under 35 U.S.C. 154(b) by 0 days.

(21) Appl. No.: 10/403,787

(22) Filed: Mar. 31, 2003

(65) Prior Publication Data

US 2004/0187611 A1 Sep. 30, 2004

(51) Int. Cl.⁷ .................................................. G01N 1/10
(52) U.S. Cl. .............................. 73/863.52; 73/864.63; 73/863.57
(58) Field of Search ..................... 73/863.52, 863.57, 73/864.63, 863.63, 863.64, 864.51; 210/512.1, 163, 164, 787, 789; 137/409, 426, 433

(56) References Cited

U.S. PATENT DOCUMENTS

| | | | |
|---|---|---|---|
| 3,296,858 A | 1/1967 | Doury et al. | |
| 4,013,091 A | * 3/1977 | Hudson | 137/414 |
| 4,732,037 A | 3/1988 | Daube, Jr. et al. | |
| 5,341,690 A | 8/1994 | Dawson et al. | 73/863.61 |
| 5,347,877 A | 9/1994 | Gadbois | 73/863.52 |
| 5,408,892 A | 4/1995 | Kawanami et al. | 73/364.33 |
| 5,413,005 A | 5/1995 | Gray | 73/863.43 |
| 5,487,314 A | 1/1996 | Phillips | 73/864.66 |
| 5,524,495 A | 6/1996 | Dudley | 73/863.52 |
| 5,587,539 A | 12/1996 | Carpenter | 73/863.52 |
| 5,744,731 A | 4/1998 | Dudley | 73/864.63 |
| 5,783,758 A | 7/1998 | Dudley | 73/863.52 |
| 5,821,437 A | 10/1998 | Budin | 73/864.63 |
| 5,847,292 A | 12/1998 | Young et al. | 73/864.63 |
| 5,915,408 A | 6/1999 | Dudley | 137/244 |
| 6,135,523 A | * 10/2000 | Pratt | 294/68.25 |
| 6,276,220 B1 | 8/2001 | Varhol | 73/863.21 |
| 2002/0092362 A1 | 7/2002 | Tonge et al. | 73/861 |

FOREIGN PATENT DOCUMENTS

GB 918161 2/1963

* cited by examiner

*Primary Examiner*—Hezron Williams
*Assistant Examiner*—Nashmiya S. Fayyaz
(74) *Attorney, Agent, or Firm*—Wood, Herron & Evans LLP (57) ABSTRACT

A liquid sample collection system includes a container having an interior reservoir for receiving the liquid sample, and a valve assembly that may be coupled to the container to facilitate collecting the liquid sample, the valve assembly includes a valve housing having a funnel-shaped inlet for directing liquid into the container and a valve that automatically closes when the container is full. The valve assembly further includes a separator configured to inhibit particulate material from entering the valve housing inlet.

19 Claims, 5 Drawing Sheets

LIQUID SAMPLE COLLECTION SYSTEM

FIELD OF THE INVENTION

The present invention relates to environmental monitoring, and more particularly to a system for collecting a sample of liquid from a liquid flow.

BACKGROUND OF THE INVENTION

In an effort to monitor and control pollutants and other contaminants entering the environment from sources such as industrial facilities, governments have enacted regulations requiring these sources to collect samples from rainwater runoff. For example, the U.S. Environmental Protection Agency (EPA) has issued rules requiring the collection of water samples from storm events that cause accumulation greater than one inch in magnitude and which occur more than 72 hours from a prior storm event that required sample collection. Generally, the collected sample is required to contain storm water runoff occurring within the first 30 minutes of a storm event, often referred to as a "grab sample." In addition to Federal regulations, many states have also established programs that require the collection of liquid samples prior to issuing permits to industrial facilities to allow them to discharge runoff into public storm drain systems.

To obtain a proper sample, a liquid collection system must be operable to collect the liquid at the onset of a storm event, and also to prevent the collection of debris or other contaminants prior to the storm event. The collection system must also be capable of stopping the collection of liquid after the 30 minute interval, otherwise undesirable dilution of the sample will occur.

Because the occurrence of storm events may be sporadic and unpredictable, it is impractical to have personnel standing by to place sample collection devices in position for the collection of liquid at the outset of a storm event. Accordingly, sampling systems have been developed which permit the automatic collection of storm water runoff without the need for human intervention. Many of these automatic collection systems include complex hardware and/or electronic monitoring equipment which are quite expensive. Other strictly mechanical systems capable of opening at the outset of a storm event are available, such as the device described in U.S. Pat. No. 5,821,437. However, these devices are also complex and thus quite costly. The financial burden that these prior storm water collection systems impose upon those who have need to use them has lead to a rather significant level of noncompliance with the government regulations. Furthermore, mechanical systems such as that described in U.S. Pat. No. 5,821,437 are susceptible to inadvertent triggering of the mechanism for opening the sample collection device prior to a storm event. While more simple systems for collecting storm water are available, these generally comprise open containers, often protected by only a grate to keep out large debris. These systems do not prevent the collection of unwanted debris which may pass through the grate and into the container prior to a storm event, and they do not prevent the accumulation of additional liquid after the grab sample has been obtained.

There is thus a need for a liquid sample collection system that overcomes drawbacks of the prior art such as those discussed above.

SUMMARY OF THE INVENTION

The present invention provides a liquid sample collection system that facilitates automatic collection of a grab sample of storm water runoff. The system includes a liquid sample collection device comprising a liquid sample collection container and a valve assembly configured to direct liquid from a storm water runoff flow into the container. The valve assembly includes a housing with a funnel-shaped inlet to help direct liquid into the container. The valve assembly further includes a valve that is operable between an open condition that permits liquid to be collected within the container, and a closed condition wherein liquid is prevented from collecting within the container. Accordingly, the closed position of the valve helps to preserve the quality of the liquid sample after it has been collected.

The valve assembly also includes a separator that is configured to direct liquid into the container while preventing particulate material from entering the container. In an exemplary embodiment, the separator has a curved surface that permits water to flow into the inlet of a valve housing and into the container. Particulate material that contacts the curved surface is deflected away from the inlet and is not collected with the liquid sample.

In another aspect of the invention, a liquid sample collection system includes a liquid sample collection device, as described above, and a receptacle for containing the liquid sample collection device during the collection of a liquid sample. Advantageously, the receptacle is configured to be positioned in a variety of environments and locations to facilitate the collection of a liquid sample.

BRIEF DESCRIPTION OF THE DRAWINGS

The features and objectives of the present invention will become more readily apparent from the following Detailed Description taken in conjunction with the accompanying drawings.

DETAILED DESCRIPTION

Figure 1:
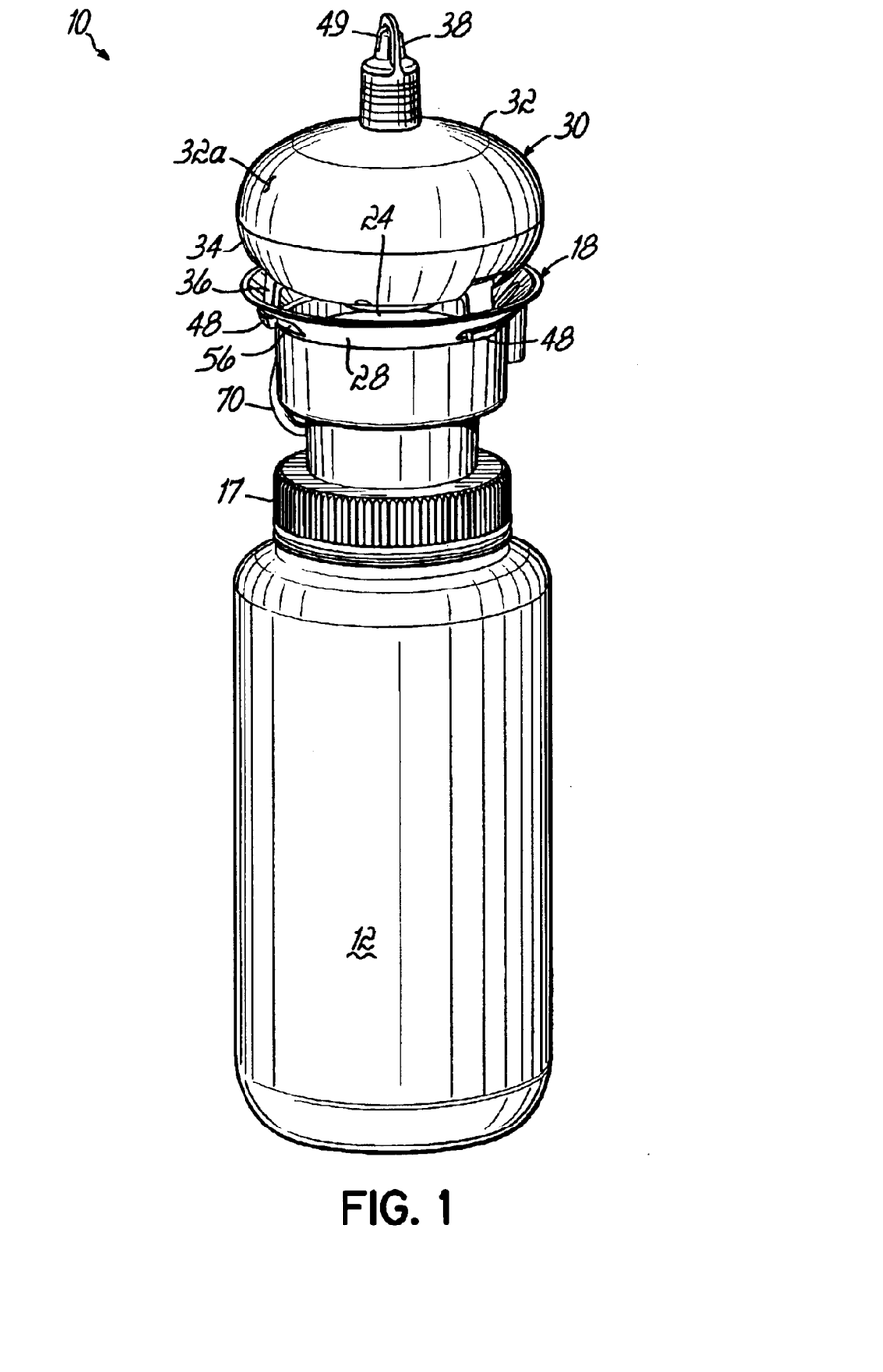
FIG. 1 is a perspective view of an exemplary liquid sample collection device according to the present invention.
Figure 2:
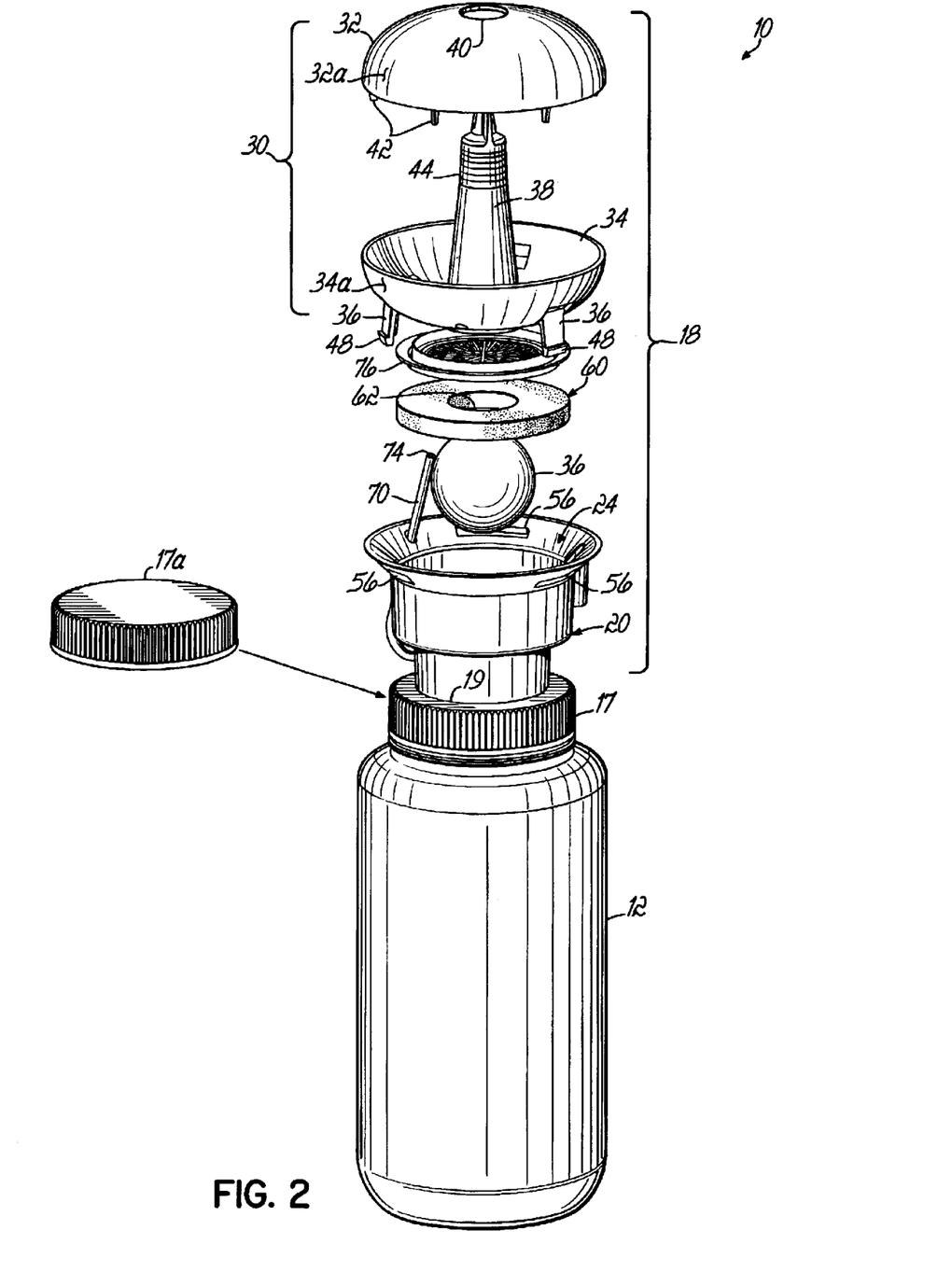
FIG. 2 is an exploded perspective view of the device of FIG. 1.
Figure 3:
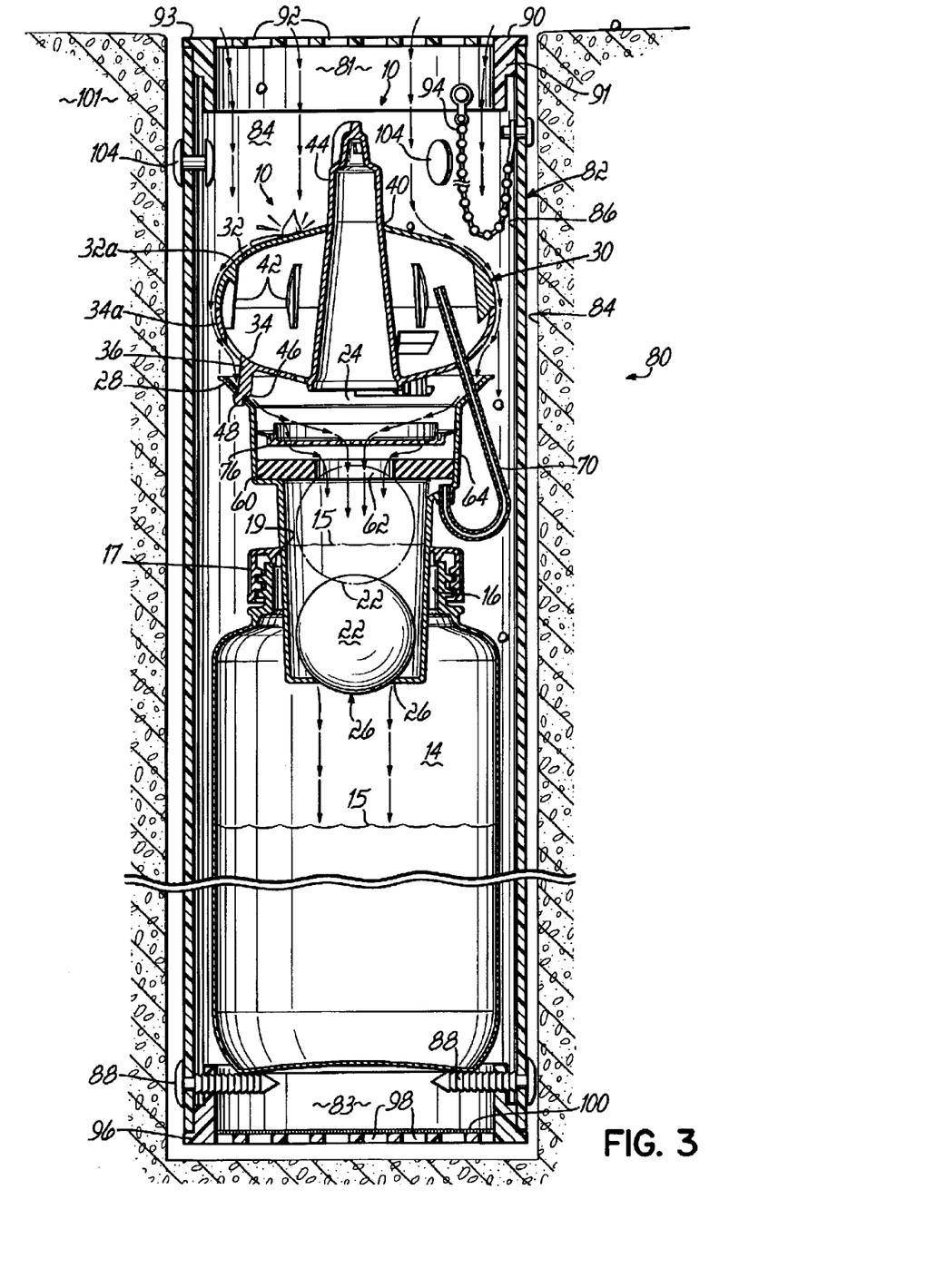
FIG. 3 is a vertical cross-sectional view of a liquid sample collection system including the sample collection device of FIG. 1.

Referring to FIGS. 1–3, there is shown an exemplary liquid sample collection device 10 of the present invention. The liquid sample collection device 10 includes a container 12 having an interior reservoir 14 and an opening 16 at the upper end thereof defined by a cylindrical neck 16a for receiving the liquid sample from a flow of liquid. The device 10 further includes a valve assembly 18 that valves liquid from the flow through the opening of the container 12 to the interior reservoir 14. In the exemplary embodiment shown, the container 12 comprises a 1-liter plastic bottle available from Nalge Nunc International, of Rochester, N.Y. The container 12, as noted, has a neck portion surrounding and defining the opening 16, which is preferably externally threaded, for receiving an internally threaded closure 17. The closure 17 has an aperture 19 sized to receive the valve assembly 18 to facilitate collection of a liquid sample. After a liquid sample has been obtained, the closure 17 may be removed and replaced with another closure 17a that does not have an aperture, whereby the liquid contents of the container 12 may be sealed.

The valve assembly 18 includes a valve housing 20 that is couplable to the container 12 for channeling the flow into the reservoir 14 and a valve operable between opened and closed conditions to thereby allow or prevent the flow of liquid through the valve housing 20. In the exemplary embodiment shown, the valve assembly 18 comprises a float 22 in the form of a buoyant ball. The float 22 is contained within the valve housing 20 between a flared, funnel-shaped upper margin 28 defining an inlet 24 and a lower outlet 26. The valve assembly 18 further includes a separator 30 configured to direct liquid through the valve housing 20 and to prevent particulate material, such as dirt, small pebbles and other debris from entering the valve housing 20.

In the exemplary embodiment shown, the separator 30 is a two-piece assembly comprising an upper member 32 and a lower member 34 that are coupled to the valve assembly 18 proximate the inlet 24 of the valve housing 20. The separator 30 has a generally ellipsoidal shape and each of the upper and lower members 32, 34 form one-half of the ellipsoidal shape. The lower member 34 has several downwardly extending legs 36, and a hollow, tubular spindle 38 which extends upwardly from a central portion of the lower member 34. A central aperture 40 formed through the upper member 32 is configured to engage the exterior of the spindle 38, whereby the upper and lower members 32, 34 may be coupled together. The upper member 32 further includes several downwardly extending ribs 42 arranged circumferentially around a lower portion of the upper member 32 to facilitate alignment and engagement of the upper member 32 with the lower member 34. The upper portion of the spindle 38 includes a series of serrations or teeth 44 formed on an outer surface thereof. The aperture 40 on the upper member 32 is sized to frictionally engage the serrations or teeth 44, whereby the upper member 32 and lower member 34 may be secured to one another by engagement of the aperture 40 with the serrations or teeth 44.

In the exemplary embodiment shown, the separator 30 is coupled to the valve housing 20 proximate inlet 24 thereof. More specifically, the downwardly extending legs 36 of the lower separator member 34 engage slots 56 formed into the flared margin 28 of valve housing 20. As depicted most clearly in FIGS. 2 and 3, shoulders 46 and tabs 48 are formed in the distal ends of legs 36. The shoulders 46 help to support the separator 30 on the flared, funnel-shaped upper margin 28 of the valve housing 20, and the tabs 48 help to secure the separator to the valve housing 20 when the legs 36 are inserted through the slots 56 in the flared upper margin 28 of the valve housing 20.

The distal end of the spindle 38 extends above the upper portion of the separator upper member 32 to permit grasping the valve assembly 18 and thereby facilitate removal of the collection device 10 from a test location. The distal end of the spindle 38 may be provided with a hole 49 formed therethrough for coupling a hook or ring (not shown) to the spindle 38 to aid in the removal of the collection device 10.

The lower member 34 of the separator 30 further includes holes 58 formed through the walls of the lower member 34 to drain liquid which may inadvertently enter the interior of the separator 30.

Figure 3A:
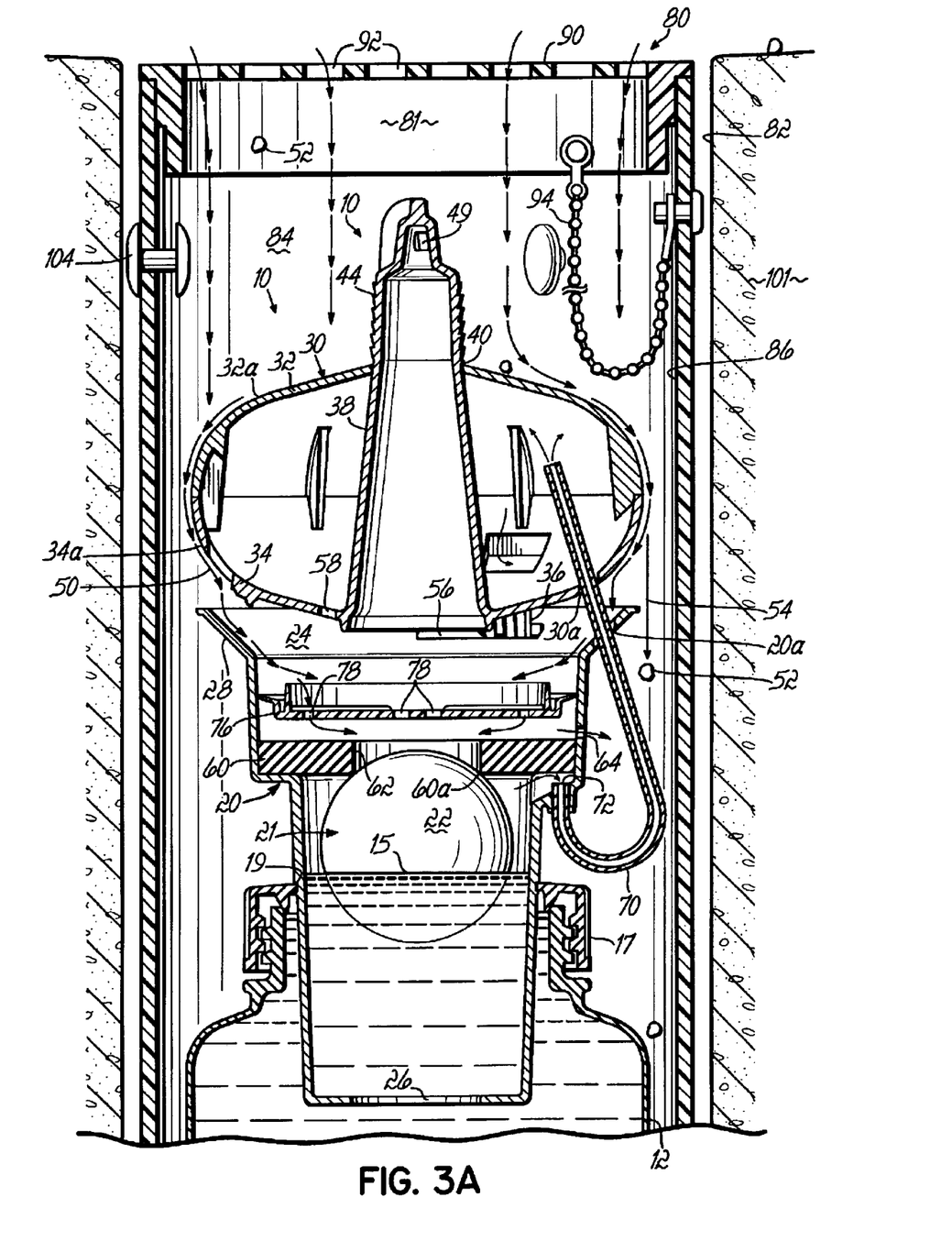
FIG. 3A is a detailed cross-sectional view of the valve assembly of FIG. 3.

As depicted in FIGS. 3 and 3A, the exterior surface of the separator 30 is curved and directs liquid into the inlet 24 of the valve housing 20, as shown by arrows 50, while causing particles, such as dirt, dust, small pebbles or other debris 52 to be deflected downwardly below the inlet 24 of the valve housing 20, as depicted by arrows 54. Specifically, as liquid impinges the surface of the separator 30, it is drawn downwardly along the outer surface 32a of the upper separator member 32 by gravity and then continues flowing downwardly and inwardly over the surface 34a of the lower separator member 34 due to the effects of surface tension in the liquid as depicted by flow path designating arrows 50. As the liquid flow proceeds along the surface 34a of the lower separator member 34, the effect of gravity on the liquid eventually exceeds the surface tension and the liquid is thereafter drawn by gravity into the funnel-shaped inlet 24 of the valve housing 20. Likewise, solid particles 52 which impinge the surface 32a of the upper separator member 32 are drawn by gravity downward over the surface 32a of the upper separator member 32, but are unable to follow the inwardly curving surface 34a of the lower separator member 34, and thus fall downwardly from the outermost peripheral section thereof, outwardly past the inlet 24 of the valve housing 20, as depicted by arrows 54, and do not enter the valve housing.

While the exemplary separator 30 of the present invention has been shown and described as having a generally ellipsoidal shape, it will be recognized that the separator 30 may have other configurations, such as a spherical shape, or other curved surface having an outwardly and downwardly extending first surface section, and an inwardly and downwardly extending second surface section, whereby the liquid flow is directed to the inlet 24 of the valve housing 20 and particulate material is diverted outwardly o the inlet 24, thereby preventing it from entering the inlet of the valve housing 20. Preferably, the outermost periphery of the separator 30 extends at least to the outermost periphery of the valve housing inlet 24, so that particles 52 falling from the separator 30 do not enter the inlet 24 and are thus prevented from being collected with the liquid sample.

With continued reference to FIGS. 3 and 3A, use of the liquid sample collection device 10 to automatically collect a sample of liquid from a liquid flow will now be discussed. The device 10 is positioned to be exposed to at least a portion of the liquid storm runoff flow such that the liquid impinges the upper surface of the separator 30 and is drawn by gravity around the surface of the separator and into the inlet 24 of the valve housing 20, while particulate material is separated from the liquid, as described above. As the liquid flows from the inlet 24 to the outlet 26 of the valve housing 20, it displaces the buoyant float 22 upwardly away from the outlet 26 of the valve housing 20, from the position shown in FIG. 3, allowing the water to pass down through the outlet 26 whereafter the liquid is collected in the interior reservoir 14 of the container 12. As the liquid 15 accumulates in the reservoir 14, the level of liquid 15 rises and eventually causes the float 22 to move upwardly toward a valve seat 60a formed within the valve housing, as illustrated in FIG. 3A. In the exemplary embodiment shown, the valve seat 60a comprises the lower circular edge of an opening 62 formed in a rubber gasket 60 positioned between the valve inlet 24 and valve outlet 26 of the valve housing 20. When the float 22 is in a position out of contact with valve seat 60a, as shown in FIG. 3, liquid flows downwardly through the hole 62 in the gasket 60 and through the outlet 26 of the valve housing 20 into the interior reservoir 14 of container 12. As the float 22 rises due to the increasing level of liquid 15 within the reservoir 14, the float 22 eventually engages the gasket 60, as shown in FIG. 3A. The float 22 engages seat 60a, whereby additional liquid is prevented from entering the reservoir 14 via opening 62 formed in gasket 60. Advantageously, the interior volume of the container 12 is sized to receive a volume of liquid from the storm runoff corresponding approximately to a 30 minute grab sample of liquid storm runoff. After the float 22 engages the valve seat, additional liquid is prevented from entering the container and the quality of the collected grab sample is maintained.

The valve housing 20 may further include a small aperture 64 (FIG. 3A) formed through the flared housing section 28 and configured to drain liquid material that may otherwise become trapped above the valve seat after the valve has been moved to a closed condition. In a preferred embodiment, the valve housing 20 is configured such that the volume of fluid remaining in the valve housing 20 after the valve has been moved to a closed position is equivalent to the volume of fluid needed to fill the container 12 after the valve housing 20 is removed. Accordingly, when the valve assembly 18 is removed from the opening of the container 12, the liquid remaining in the valve housing 20 drains into the interior reservoir 14 to completely fill the container 12.

With continued reference to FIG. 3A, the valve assembly 18 further includes a vent in communication with the interior reservoir 14 to permit air which initially resides in the reservoir 14 to be purged from the container 12 as liquid fills the reservoir 14. In the exemplary embodiment shown, the vent comprises a conduit 70 having a first end 72 coupled to the interior of the valve housing 20 via a port in the wall thereof, which in turn communicates with the interior reservoir 14 through the valve housing outlet 26. The conduit 70 extends upwardly from the valve housing 20 and into the interior of the separator 30, via an opening 20a in the valve housing and an opening 30a in the lower separator member 34, whereby a second end 74 of the conduit 70 positioned within the separator 30 is protected from exposure to liquid or debris which might otherwise plug the conduit 70. The first end 72 of the conduit 70 is positioned adjacent the outer wall of the valve housing 20 and is located in an area beneath the gasket 60 whereby the first end 72 is also protected from liquid and debris. Advantageously, air displaced by the liquid, as it fills the interior reservoir 14, may flow through the valve housing 20, into the first end 72 of the conduit 70, through the conduit 70, and out the second end 74.

The valve assembly 18 may further include a disc-shaped filter 76 disposed within the valve housing 20 and upstream of the valve seat 60a. The filter 76 includes a series of holes 78 formed therethrough to permit liquid to pass through the filter 76, but prevent particulate from entering the interior reservoir 14. The filter 76 has a peripheral edge which frictionally engages the interior wall surface of the valve housing 20 above the valve seat 60a. Advantageously, the holes 78 formed through the filter 76 are sized and arranged to filter out or screen particles exceeding a specified size, as desired. In another exemplary embodiment (not shown), the filter comprises a porous membrane whereby even very fine particles may be filtered out or screened from the liquid flowing through the valve housing 20 into the reservoir 14. The filter may also be used to control the flow rate of liquid through the valve housing 20, whereby large holes may be used to provide a rapid flow through the valve housing 20 and a corresponding quick-fill of the reservoir 14. Smaller holes, or porous membranes, may be used to provide slower flow through the valve housing 20 and a corresponding slow accumulation of liquid in the interior reservoir 14 of the container 12.

Advantageously, the filter 76 operates to prevent particles from entering the container 12 and contaminating the liquid sample. Accordingly, the liquid sample collection device 10 may alternatively be used without the separator 30, whereby the filter 76 functions to screen particles from the incoming flow. In another exemplary embodiment, the liquid sample collection device 10 may be used without either the filter 76 or the separator 30, for example, when it is desired to collect a sample which includes particle material entrained in the incoming liquid storm runoff.

In the exemplary embodiment shown in FIG. 3, the liquid sample collection system 80 of the present invention further includes a receptacle 82 for housing the liquid sample collection device 10 for collection of a liquid sample. The receptacle 82 has an inlet 81, an outlet 83 and an interior chamber 84 sized to receive the container 12 and the valve assembly 18, whereby the container 12 and valve assembly 18 may be removably placed within the receptacle 82 for collection of a liquid sample. In the exemplary embodiment shown, the receptacle 82 comprises a plastic tube having an inner diameter 86 sized to receive the container 12 and valve assembly 18. Several studs 88 extending inwardly through the sidewalls of the receptacle 82 provide a support for the container 12 and valve assembly 18, whereby the container 12 and valve assembly 18 may be positioned within the receptacle 82 at a desired depth beneath the receptacle inlet 81.

The liquid sample collection system 80 further includes a cover 90 that is removably received over the receptacle inlet 81. The cover 90 includes a downwardly extending skirt section 91 which is received within the receptacle inlet 81 to frictionally engage the receptacle at the inner diameter 86, and an outwardly extending flange section 93 configured to engage the end of the receptacle 82, proximate the inlet 81, to prevent the cover 90 from being forced within the receptacle 82. The cover 90 includes at least one aperture 92 formed therethrough for permitting liquid to enter the inlet 81 of the receptacle 82 and to block large particles, such as branches, stones, or other debris from entering the receptacle 82. In the exemplary embodiment shown, the cover 90 is tethered to the receptacle 82 by a chain 94 to help prevent loss of the cover 90 while the liquid sample collection device 10 is being accessed, or in the event the cover 90 is inadvertently separated from the receptacle 82. The outlet 83 of the receptacle 82 is configured to permit liquid that was not collected in the container 12 to pass out of the receptacle 82.

In the exemplary embodiment shown, the receptacle further includes a drain cap 96 coupled to the receptacle proximate the outlet 83. The drain cap 96 has a construction similar to the cover 90, with apertures 98 formed through the drain cap 96 to permit liquid material to pass through the receptacle outlet 83. The drain cap 96 is secured to the receptacle 82 by the studs 88 which support the liquid sample collection device 10 within the receptacle 82. A mesh screen 100 may also be disposed within the receptacle 82, proximate the outlet 83, to further filter liquid passing through the receptacle 82.

Advantageously, the receptacle 82 is configured to be positioned in a variety of environments to facilitate the collection of a liquid sample. In one exemplary embodiment shown in FIG. 3, the receptacle 82 may be located in the ground 101 such that the inlet 81 of the receptacle 82 and the cover 90 are at, or slightly below, grade. This configuration may be useful for facilitating the collection of liquid flowing over the ground surface of a test area. The receptacle outlet 83 may also be in communication with a drain system (not shown) to prevent the accumulation of liquid within the receptacle 82.

Figure 4:
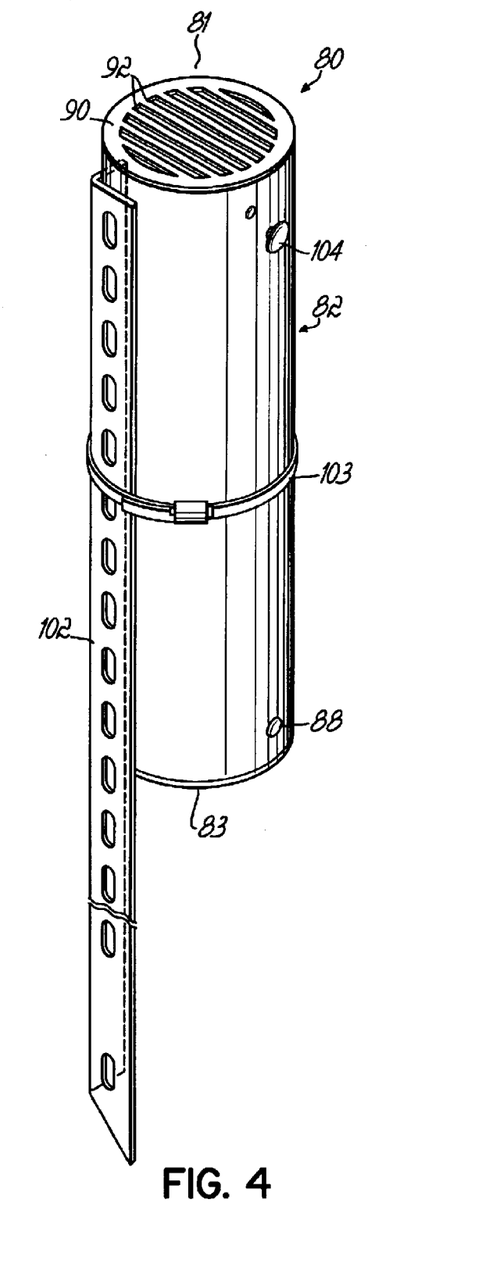
FIG. 4 is a perspective view of an exemplary liquid sample collection system of the present invention.

In another exemplary embodiment shown in FIG. 4, the receptacle 82 may be secured to a stake or post 102 using a strap 103 for example, such that the receptacle 82 is positioned above ground level. Positioning the receptacle 82 in this manner may be beneficial, for example, when the storm runoff is expected to provide a relatively deep flow and it is desired to obtain a sample of liquid from a portion of the flow substantially above ground level. When the liquid sample collection system 80 is used in this manner, the drain cap 96 and mesh screen 100 help to prevent unwanted debris in the storm runoff from entering the receptacle 82 through the outlet 83.

Figure 5:
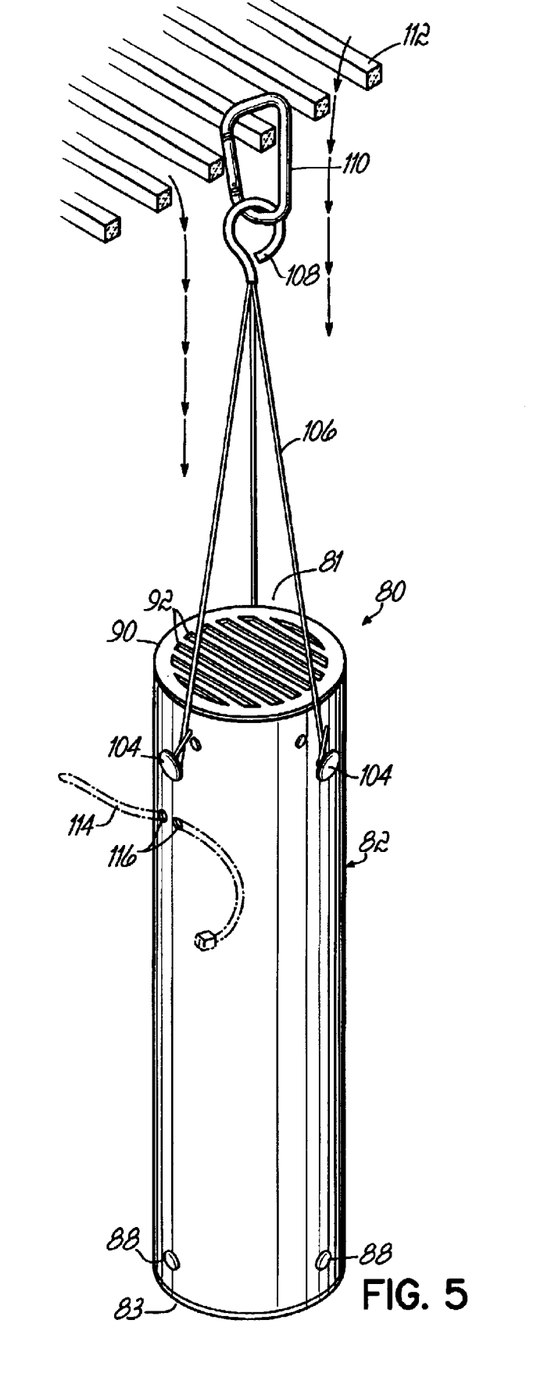
FIG. 5 is a perspective view of another exemplary liquid sample collection system of the present invention.

The receptacle 82 may also be configured to be suspended in a hanging manner from a support positioned above the receptacle 82, as depicted in FIG. 5. In an exemplary embodiment, the receptacle 82 includes several panel fasteners 104 installed circumferentially around the receptacle 82 to provide structure for coupling the receptacle 82 to a harness 106. The harness 106 includes a hook 108 for suspending the receptacle 82 from the support, such as the grate 112 of a sewer drain. The harness 106 may also include a spring loaded clip 110 to facilitate securing the harness 106 to and removing the harness 106 from the support. This configuration may be advantageous for collecting a liquid sample from a storm runoff flow which passes over a grate 112 to a sewer system. The receptacle 82 may also be provided with a tie strap 114, coupled to the receptacle 82 through holes 116 formed in the sides of the receptacle 82, to facilitate securing the receptacle to structure, such as a post or pipe, so that the location of the receptacle 82 may be controlled.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A valve assembly for a liquid sample collection device including a container having a interior reservoir for receiving the liquid sample from a flow of liquid, the valve assembly comprising:

a valve housing couplable to the container for channeling the flow of liquid into the reservoir of the container, said valve housing having an inlet for exposure to the flow and an outlet in communication with the reservoir;

a valve located within said valve housing and operable between open and closed conditions, said open condition permitting liquid to pass through said valve housing, said closed condition preventing the passage of liquid through said valve housing; and a separator cooperating with said valve housing inlet and configured to direct liquid through said valve housing via said inlet and to divert particulate material outwardly of said inlet of said valve housing;

said separator including a surface spaced above and extending at least entirely over said valve housing inlet;

said surface including a peripheral surface region extending downwardly and inwardly above said valve inlet such that liquid falling on said surface flows along said peripheral surface region and then into said valve inlet.

2. The valve assembly of claim 1, wherein said valve housing inlet has a converging section.

3. The valve assembly of claim 1, wherein said valve comprises a float and a valve seat disposed within said valve housing, said float configured to be displaced between unseated and seated engagement relative to said valve seat by liquid received in the container reservoir to thereby move said float between said open condition and said closed condition, respectively.

4. The valve assembly of claim 1, wherein said surface is configured to direct liquid into said valve housing inlet and to cause particulate material to bypass said velve housing inlet.

5. The valve assembly of claim 4, wherein said separator surface comprises a curved surface disposed proximate said valve housing inlet, said curved surface shaped to direct liquid into said valve housing inlet and to cause particulate material to bypass said inlet.

6. The valve assembly of claim 4, wherein said surface comprises a downwardly and outwardly extending upper surface section, and a downwardly and inwardly extending lower surface section.

7. The valve assembly of claim 4, wherein said surface has a first outermost periphery and said valve housing has a second outermost periphery, wherein said first outermost periphery extends outwardly to at least to said second outermost periphery to inhibit particulate material from entering said valve housing inlet.

8. The valve assembly of claim 5, wherein said separator has a generally ellipsoidal shape.

9. The valve assembly of claim 1, further comprising a filter disposed within said valve housing and configured to permit the flow of liquid through said valve housing white inhibiting particulate material from passing through said valve housing.

10. The valve assembly of claim 1, further comprising a vent in communication with the container reservoir when said valve assembly is coupled to the container, and configured to permit gas displaced by liquid received in the container reservoir via said valve to escape from the container reservoir.

11. The valve assembly of claim 10, wherein said vent comprises a conduit communicating with the container reservoir via said valve housing outlet.

12. The valve assembly of claim 1, further comprising an aperture disposed in said valve assembly to drain liquid that enters said inlet after said valve is in said closed condition.

13. A liquid sample collection system, comprising:

a container configured to receive a sample of liquid through an inlet opening therein; and a valve assembly couplable to said container via said container inlet opening, said valve assembly comprising:

a valve housing in liquid communication with said container inlet opening, and configured to channel a flow of liquid into said container, said valve housing having a valve inlet and an outlet, a valve located within said valve housing and operable between open and closed conditions, said open condition permitting liquid to pass through said valve housing into said container via said container inlet opening, said closed condition preventing the passage of liquid through said valve housing, and a separator cooperating with said valve inlet and configured to direct liquid through said valve housing via said housing inlet and to divert particulate material outwardly of said inlet of said valve housing;

said separator including a surface spaced above and extending at least entirely over said valve housing inlet;

said surface including a peripheral surface region extending downwardly and inwardly above said valve inlet such that liquid failing on said surface flows along the peripheral surface region and then into said valve inlet.

14. The liquid sample collection system of claim 13, further comprising:

a receptacle having an interior chamber sized to receive said container and said valve assembly, and having a receptacle inlet and a receptacle outlet in communication with said interior chamber, said receptacle configured to removably support said container and said valve assembly within said interior chamber; and a cover removably coupled to said receptacle proximate said receptacle inlet, said cover having at least one aperture formed therethrough for permitting the flow of liquid into said interior chamber via said receptacle inlet, and for preventing non-liquid debris from entering said interior chamber via said receptacle inlet.

15. The liquid sample collection system of claim 14, further comprising:

a harness couplable to said receptacle and configured to suspend said receptacle from a support positioned above said receptacle.

16. The liquid sample collection system of claim 14, further comprising a mounting member adapted for engagement with a ground surface, said mounting member couplable to said receptacle to support said receptacle a distance above the ground surface.

17. A valve assembly for a liquid sample collection device including a container having a interior reservoir for receiving the liquid sample from a flow of liquid, the valve assembly comprising:

a valve housing couplable to the container for channeling the flow of liquid into the reservoir of the container, said valve housing having an inlet for exposure to the flow and an outlet in communication with the reservoir;

a valve located within said valve housing and operable between open and closed conditions, said open condition permitting liquid to pass through said valve housing, said closed condition preventing the passage of liquid through said valve housing; and a separator cooperating with said valve housing inlet and having a curved, substantially solid surface configured to direct liquid into said valve housing inlet and to divert particulate material outwardly of said valve housing inlet;

wherein said separator directs liquid into said valve housing by surface tension between the liquid and said substantially solid surface of said separator.

18. A valve assembly for a liquid sample collection device including a container having a interior reservoir for receiving the liquid sample from a flow of liquid, the valve assembly comprising:

a valve housing couplable to the container for channeling the flow of liquid into the reservoir of the container, said valve housing having an inlet for exposure to the flow and an outlet in communication with the reservoir;

a valve located within said valve housing and operable between open and closed conditions, said open condition permitting liquid to pass through said valve housing, said closed condition preventing the passage of liquid through said valve housing; and a separator cooperating with said valve housing inlet and configured to direct liquid through said valve housing, via said inlet and to divert particulate material outwardly of said inlet of said valve housing;

wherein said separator directs liquid through said valve housing by surface tension between the liquid and said separator.

19. A valve assembly for a liquid sample collection device including a container having a interior reservoir for receiving the liquid sample from a flow of liquid, the valve assembly comprising:

a valve housing couplable to the container for channeling the flow of liquid into the reservoir of the container, said valve housing having an inlet for exposure to the flow and an outlet in communication with the reservoir;

a valve located within said valve housing and operable between open and closed conditions, said open condition permitting liquid to pass through said valve housing, said closed condition preventing the passage of liquid through said valve housing; and a separator cooperating with said valve housing inlet and configured to direct liquid through said valve housing via said inlet and to divert particulate material outwardly of said inlet of said valve housing;

said separator comprising a curved surface disposed proximate said valve housing inlet, said curved surface shaped to direct liquid downwardly and inwardly along said surface and then into said valve housing inlet, and to cause particulate material to bypass said inlet.

* * * * *

UNITED STATES PATENT AND TRADEMARK OFFICE
CERTIFICATE OF CORRECTION

PATENT NO. : 6,976,398 B2 Page 1 of 1
DATED : December 20, 2005
INVENTOR(S) : Leoncavallo et al.

It is certified that error appears in the above-identified patent and that said Letters Patent is hereby corrected as shown below:

<u>Title page,</u>
Item [57], ABSTRACT,
Line 4, reads "...to facilitate collecting the liquid sample, the valve assembly includes a..." and should read -- ...to facilitate collecting the liquid sample. The valve assembly includes a... --.

<u>Column 4,</u>
Line 30, reads "...material is diverted outwardly o the inlet..." and should read -- ...material is diverted outwardly of the inlet... --.

<u>Column 8,</u>
Line 10, reads "...to bypass said velve housing inlet." and should read -- to bypass said valve housing inlet. --.
Line 24, reads "...extends outwardly to at least to said second..." and should read -- ...extends outwardly to at least said second... --.
Line 31, reads "...through said valve housing white inhibiting..." and should read -- ...through said valve housing while inhibiting... --.

<u>Column 10,</u>
Line 18, reads "...through said valve housing, via said inlet..." and should read -- ...through said valve housing via said inlet... --.

Signed and Sealed this

Twenty-eighth Day of March, 2006

JON W. DUDAS
*Director of the United States Patent and Trademark Office*